(12) United States Patent
Klein et al.

(10) Patent No.: US 7,851,204 B2
(45) Date of Patent: Dec. 14, 2010

(54) CLOSURE FOR MILLILITER SCALE BIOREACTOR

(75) Inventors: David L. Klein, Palo Alto, CA (US); Robert D. Laidlaw, Albany, CA (US); Gregory Andronaco, Palo Alto, CA (US); Stephen G. Boyer, Moss Beach, CA (US)

(73) Assignee: Pall Microreactor Technologies, Inc., Mountain View, CA (US)

( * ) Notice: Subject to any disclaimer, the term of this patent is extended or adjusted under 35 U.S.C. 154(b) by 1207 days.

(21) Appl. No.: 11/450,855

(22) Filed: Jun. 9, 2006

(65) Prior Publication Data
US 2008/0014629 A1 Jan. 17, 2008

(51) Int. Cl.
*C12M 1/34* (2006.01)
*C12M 3/00* (2006.01)

(52) U.S. Cl. ................... 435/287.2; 435/305.3

(58) Field of Classification Search ........... 435/6, 435/287.1–287.3, 288.5–288.7, 305.1–305.3
See application file for complete search history.

(56) References Cited

U.S. PATENT DOCUMENTS

| | | | | | |
|---|---|---|---|---|---|
| 3,326,401 | A | * | 6/1967 | De Long | 215/308 |
| 5,180,073 | A | * | 1/1993 | Fay et al. | 215/261 |
| 5,989,924 | A | * | 11/1999 | Root et al. | 436/518 |
| 6,106,783 | A | * | 8/2000 | Gamble | 422/102 |
| 6,193,088 | B1 | * | 2/2001 | Vincent et al. | 215/261 |
| 6,376,233 | B1 | | 4/2002 | Wolf et al. | 435/288.4 |
| 6,436,351 | B1 | * | 8/2002 | Gubernator et al. | 422/102 |
| 6,500,390 | B1 | * | 12/2002 | Boulton et al. | 506/43 |
| 6,602,716 | B1 | | 8/2003 | Klimant | 436/172 |

(Continued)

FOREIGN PATENT DOCUMENTS

EP 0 976 453 2/2000

(Continued)

OTHER PUBLICATIONS

Liebsch et al "Luminescence Lifetime Imaging of Oxygen, pH, and Carbon Dioxide Distribution Using Optical Sensors" in Applied Spectroscopy vol. 54, No. 4, 2000 pp. 548-559.

(Continued)

*Primary Examiner*—Walter D Griffin
*Assistant Examiner*—Shanta G Doe
(74) *Attorney, Agent, or Firm*—Leydig, Voit & Mayer, Ltd.

(57) ABSTRACT

A closure for a microreactor includes a cap that is configured to be inserted into a well of the microreactor. The cap, or at least a portion of the cap, is compliant so as to form a seal with the well when the cap is inserted. The cap includes an aperture that provides an airway between the inside of the well to the external environment when the cap is inserted into the well. A porous plug is inserted in the aperture, e.g., either directly or in tube that extends through the aperture. The porous plug permits gas within the well to pass through the aperture while preventing liquids from passing through to reduce evaporation and preventing microbes from passing through to provide a sterile environment. A one-way valve may also be used to help control the environment in the well.

23 Claims, 4 Drawing Sheets

U.S. PATENT DOCUMENTS

| | | | |
|---|---|---|---|
| 6,673,532 B2 | 1/2004 | Rao | 435/4 |
| 2003/0235519 A1* | 12/2003 | Sha et al. | 422/102 |
| 2004/0077075 A1 | 4/2004 | Jensen et al. | 435/297.2 |
| 2005/0164373 A1 | 7/2005 | Oldham et al. | |
| 2005/0176155 A1 | 8/2005 | Klein et al. | 436/163 |

FOREIGN PATENT DOCUMENTS

| | | |
|---|---|---|
| EP | 1 069 181 | 1/2001 |
| EP | 1 122 181 | 8/2001 |
| EP | 1 580 261 A1 | 9/2005 |
| GB | 02344 | 0/1911 |
| GB | 654 541 | 6/1951 |
| WO | WO 99/20394 | 4/1999 |
| WO | WO 02/26377 | 4/2002 |

OTHER PUBLICATIONS

M.M.Maharbiz, et al.,"Microbioreactor Arrays with Parametric Control for High-Throughput Experimentation" Biotechnology and Bioengineering, vol. 85, No. 4, Feb. 20, 2004, p. 376-381.

N. Szita, et al., "Monitoring of Cell Growth, Oxygen, and pH in Microfermentors" in Micro Total Analysis Systems (m-TAS) 2002, Y. Baba, S. Shoji, and A. van den Berg (Eds.). Kluwer, Dordrecht, The Netherlands, 2002, pp. 7-9, as downloaded from http://jensengroup.mit.edu/new_students on Feb. 10, 2004.

Michel Martin Maharbiz, "Electrochemical Gas Generation for Cell Culture", PhD Dissertation, University of California Berkeley, May 2003, pp. 1-170.

Michel M. Maharbiz et al., "A Microfabricated Electrochemical Oxygen Generator for High-Density Cell Culture Arrays", Solid-State Sensor, Actuator and Microsystems Workshop, Hilton Head Island, SC, Jun. 2-6, 2002, pp. 259-264.

Shabbir B. Bambot, et al., "Potential applications of lifetime-based, phase-modulation fluorimetry in bioprocess and clinical monitoring", Tibtech Mar. 1995 (vol. 13), pp. 106-115.

European Search Report mailed Oct. 11, 2007, for EP Application 07109914.7, which claims priority to U.S. Appl. No. 11/450,855.

* cited by examiner

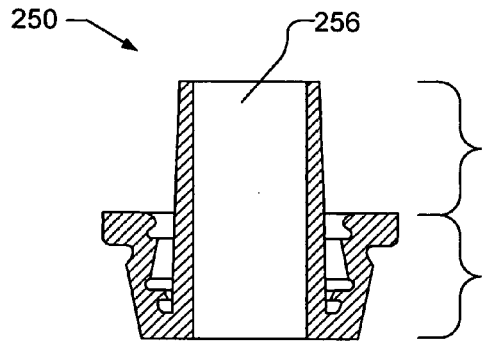
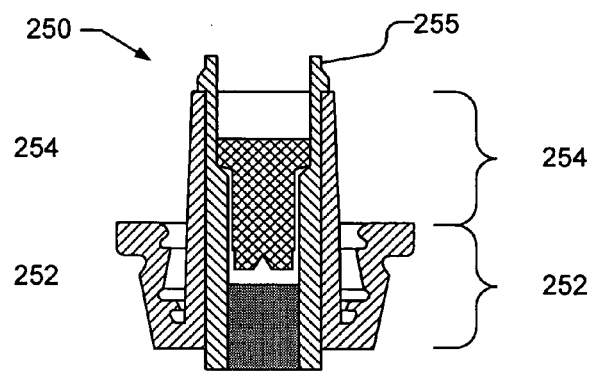
Fig. 8A
Fig. 8B
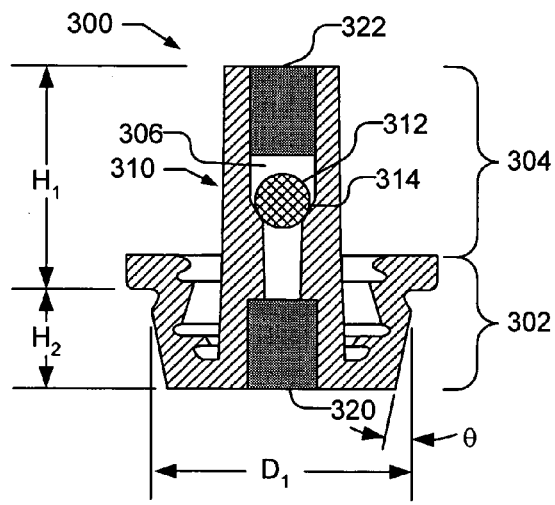
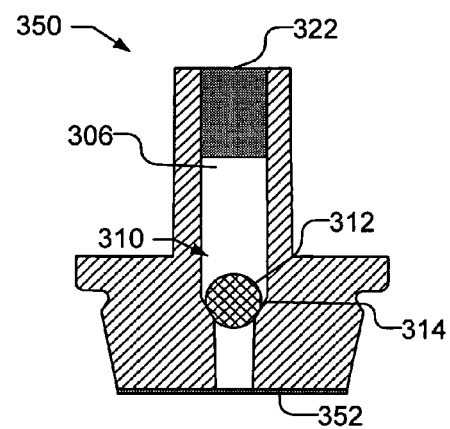
Fig. 9A
Fig. 9B
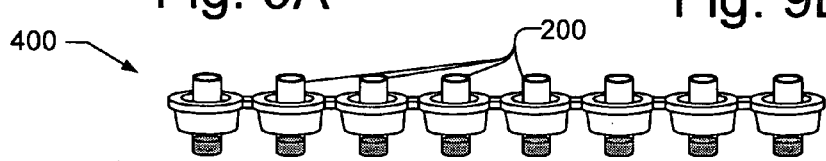
Fig. 10A
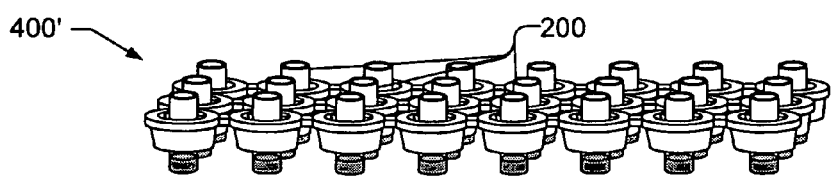
Fig. 10B

US 7,851,204 B2

CLOSURE FOR MILLILITER SCALE BIOREACTOR

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of contract No. DE-FG02-04ER83963 awarded by the Department of Energy (DOE).

FIELD OF THE INVENTION

The present invention relates to small-scale bioreactors, sometimes referred to as microreactors, and in particular to a method and apparatus for sealing microreactors and similar types of devices.

BACKGROUND

Cell culture and fermentation have value for many aspects of industrial production, such as pharmaceuticals, industrial enzyme production (e.g. detergents, food additives, textile processing, pulp and paper processing, grain processing incl. production of high fructose corn syrup), potable and fuel ethanol, amino acids, vitamins, feed additives, and many others. The actual organisms in the fermenter may vary greatly and can include a variety of bacteria, yeast, fungi, insect cells, mammalian cells, and others.

Conventionally, complex large-scale fermentation (hundreds of thousands of liters) systems are used for production. Large scale systems are manufactured by companies, such as Applikon, B. Braun, and New Brunswick Scientific. Typically, large scale cell culture and fermentation systems must be capable of: 1) feeding the media with nutrients, 2) measuring and changing the Oxygen level, 3) measuring and changing the temperature, 4) measuring and changing the pH level, 4) stirring the contents, 5) purging byproducts (such as $CO_2$), and 6) monitoring the reaction quality (such as cell density and protein expression).

Before scaling up reactions in large capacity fermenters, similar reactions are typically performed at a smaller scale. Small-scale fermenters, e.g., in the 1-20 liter range, provide most if not all of the desired performance functions of the large scale fermenters described above. However, the small-scale fermenters are expensive, and have a relatively larger form than necessary for many desired applications.

For fermentations on a smaller scale, less expensive systems are used. Small-scale bioreactors ("microreactors") are a tool of growing value to the microbiology community. They are used for screening of new strains, optimization of culture conditions, and for micro-scale production.

Due to the sensitivity of the reactions and measurements performed in microreactors, it is necessary to carefully control the environment in the wells of the microreactor. Accordingly, improvements on the control of the environment of the microreactors are desirable.

SUMMARY

In accordance with an embodiment of the present invention, a closure for a microreactor may provide a sterile environment while reducing evaporation. The closure includes a cap that is configured to be inserted into a well of the microreactor. The cap, or at least a portion of the cap, is compliant so as to form a seal with the well when the cap is inserted. The cap includes an aperture that provides an airway between the inside of the well to the external environment when the cap is inserted into the well. A porous plug is inserted in the aperture, e.g., either directly or in tube that extends through the aperture. The porous plug permits gas within the well to pass through the aperture while preventing liquids from passing through to reduce evaporation and preventing microbes from passing through to provide a sterile environment. A one-way valve may also be used to help control the environment in the well.

BRIEF DESCRIPTION OF THE DRAWINGS

FIG. 8A illustrates a cross-sectional view of a cap that may be used with the closure, in accordance with an embodiment of the present invention.

FIG. 8B illustrates the cap from FIG. 8A with a one-way valve inserted through the central aperture.

FIGS. 9A and 9B illustrate other closures, in accordance with embodiments of the present invention.

FIGS. 10A and 10B illustrate one-dimensional and two-dimensional mats, respectively, composed of a plurality of closures.

DETAILED DESCRIPTION

Figure 1A:
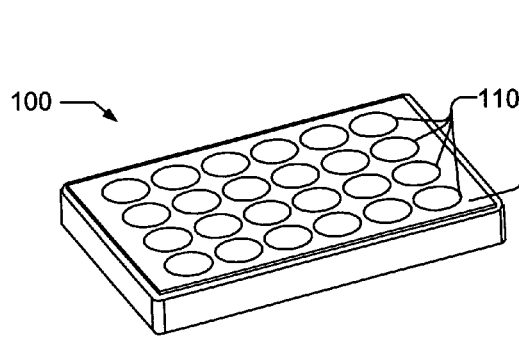
FIG. 1A illustrates a top perspective view of a microreactor with which a closure according to an embodiment of the present invention may be used.
Figure 1B:
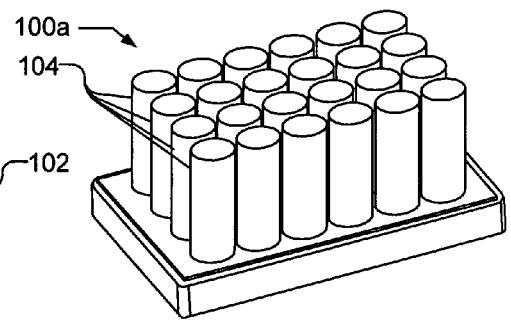
FIG. 1B illustrates a top perspective view of a microreactor with extensions with which a closure according to an embodiment of the present invention may be used.

FIG. 1A illustrates a top perspective view of a microreactor 100, sometime referred to herein as a well plate, with which a closure, in accordance with an embodiment of the present invention may be used. Well plate 100 is illustrated as having a top surface 102 and a plurality of wells 110 (sometimes referred to as an individual reactor). A well plate 100 may have, e.g., 24, 48, 96 or any other desired number of wells that extend generally downward from the top surface 102. One suitable well plate is described in U.S. Ser. No. 10/777,581, filed on Feb. 11, 2004, having Publication No. 2005/0176155, having the same assignee as the present disclosure and which is incorporated herein by reference. Alternatively, the dimensions and form of well plate 100 may be similar to the type purchased from Corning Costar from Acton, Massachusetts, as part number #3527 or from Nalge Nunc International from Rochester, New York, as part number 142485. Other types of well plates and configurations and dimensions may be used if desired. Typically, but not always, tube extensions are used with a well plate to increase the working volume of the well. For example, the total volume of a well 110 in well plate 100 is 2.5 ml. The working volume of a well is generally much reduced, e.g., to on the order of 1 ml or less, due to typical operating conditions of a microreactor, such as agitation and gas transfer. FIG. 1B illustrates a well plate 100a, which is similar to the well plate 100 in FIG. 1A, except that tube extensions 104 are glued or molded over the well plate for forming the wells. For the sake of inclusiveness, a well is defined as a well 110 and a tube extension 104 as well as a well 110 without the extension. The tube extensions 104 may increase the total volume of an individual reactor to, e.g., 10 ml. The tube extensions 104 are particularly useful with the introduction of a closure, in accordance with an embodiment of the present invention, which extends into the well, thereby further reducing working volume.

Figure 2:
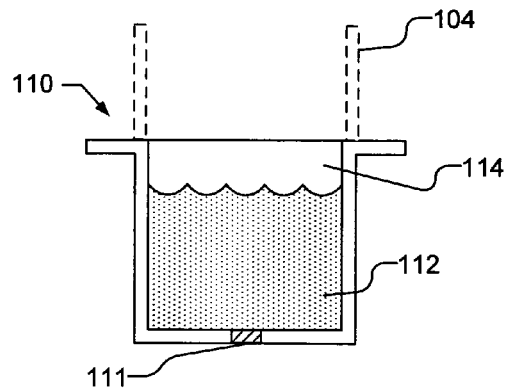
FIG. 2 illustrates a cross-sectional view of a single well in a microreactor.

FIG. 2 illustrates a cross-sectional view of a single well 110 in a microreactor, such as microreactor 100a with a tube extension 104. Well 110 is illustrated as containing a sample 112 and head space 114 above the sample 112. As discussed above, the well 110 may have a volume of 2.5 ml and a working volume of approximately 1 ml. With the extension 104 the working volume of the well 110 is increased to approximately 4 ml-5 ml. Of course, the dimensions of the extension 104 (or the well 110) may be varied to produce a desired volume, e.g., up to approximately 100 ml. During some experiments, which may be conducted over an extended period of time, e.g., 24-200 hours, the health and production rate of bacteria or cell cultures are measured, which requires a sterile enviromnent. Moreover, it is often desirable for the environment to be closely controlled for such parameters as temperature, pH, and dissolved oxygen. The well 110 may include elements, such as a gas inlet port 111 to aid in control of such parameters, which is described, e.g., in Publication No. 2005/0176155.

Figure 3:
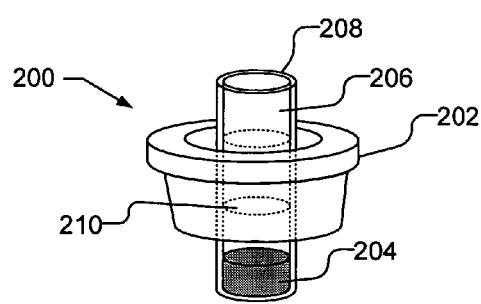
FIG. 3 illustrates a simplified side perspective view of a closure.
Figure 4:
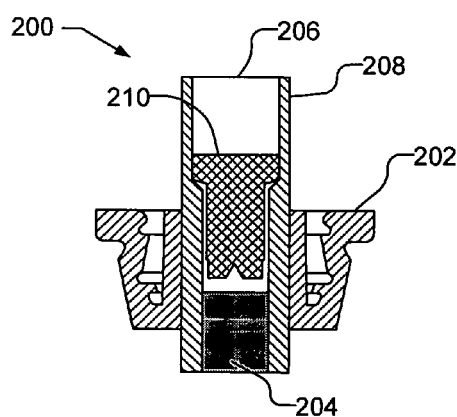
FIG. 4 illustrates a cross-sectional view of a closure, in accordance with an embodiment of the present invention.
Figure 5:
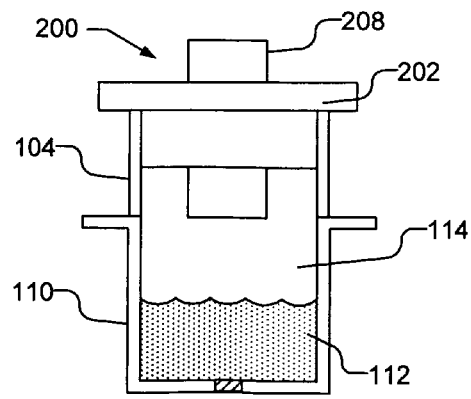
FIG. 5 illustrates a closure inserted into a well to form a seal.

FIG. 3 illustrates a simplified side perspective view of a closure 200, while FIG. 4 illustrates a cross-sectional view of a closure 200, in accordance with an embodiment of the present invention. The closure 200 is used with an individual microreactor, such as a well 110. The closure 200 can be pushed into an individual well 110 to seal the well 110, as illustrated in FIG. 5. In one embodiment, the closure 200 includes a cap 202, a porous plug 204 and a one way valve 206.

The cap 202 can be made of a compliant material such as silicone or rubber. The cap 202 is formed so that it will make a removable air-tight seal with the sidewalls of the well 110 in the microreactor 100. Thus, cap 202 can be used to seal the well 110, as well as permit access to the well 110, e.g., for loading of the well 110 with the sample 112 and eventually removing the sample 112 from the well at the end of an experiment. Moreover, cap 202 can be removed from the well to permit the introduction of material during the experiment e.g. additional water, food (glucose), nutrients and/or the remove of material. Cap 202 may be manufactured from molded silicone or rubber. A suitable cap may be purchased from Axygen Scientific Inc. of Union City, Calif. If desired, the cap 202 may have other configurations. For example, the cap 202 may be made from a non-compliant material, such as a plastic, and have a rubber or silicone O-ring that is used to produce an air-tight seal with the well 110.

The porous plug 204 is made of a plastic cylinder that is approximately 0.2 inch in diameter and 0.2 inch in length. The plug 204 can be made from a number of plastics, such as polyethylene, polytetrafluoroethylene (PTFE), as well as polypropylene, Polyvinylidene Fluoride, polyamines, and polyurethane. With the above dimensions, polyethylene and PTFE having a porosity of 5 $\mu$m to 50 $\mu$m, which have been shown to be a suitable sterile barrier. However, for increased sterility, or for porous plugs 204 with decreased length, a smaller porosity may be desirable, e.g., 0.2 $\mu$m to 5 $\mu$m, or less than 0.2 $\mu$m. A suitable porous plastic can be purchased, e.g., from Porex Corporation of Fairburn, Ga, e.g., as part number 7724. Other Porex Corp. parts may be used depending on desired tolerance, size and material.

The porous plug 204 permits gasses to pass through with a minimum of resistance, and yet inhibits liquids and microbes from passing through. The porous plug 204 permits gas to pass through with only a slight overpressure, but does not allow significant passive gas flow, which reduces evaporative losses. A closure 200 with a porous plug 204 closing a well 110, in which no gas is introduced, has been found to have is little as 0.008 ml/day of evaporative loss, while when purging gas is introduced at a constant rate of approximately 20 ml/s there is an evaporative loss of 0.59 ml/day. Accordingly, the porous plug 204 helps to reduce evaporative losses, while permitting control of the environment.

Figure 6:
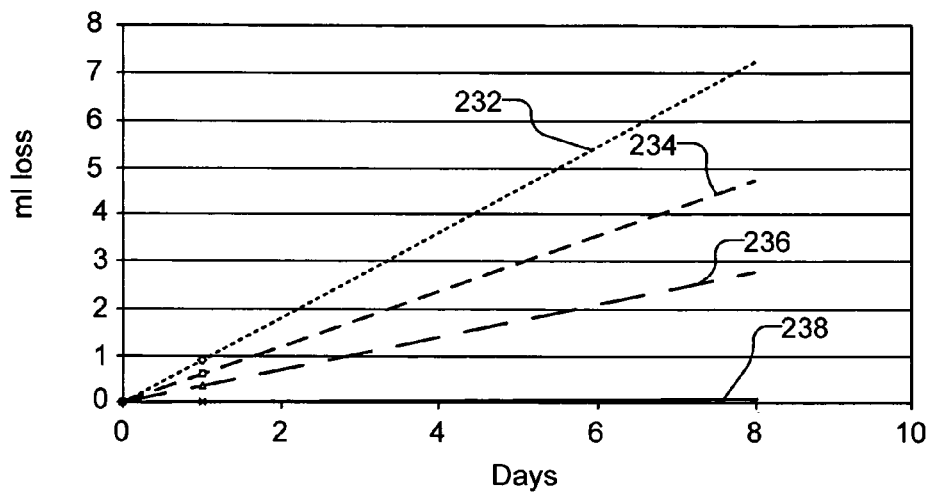
FIG. 6 is a graph showing the evaporative loss in milliliters (ml).

FIG. 6 is a graph showing the evaporative loss in milliliters (ml). The lines 232 and 234 represent the evaporative loss from a 5 ml sample of deionized water in 10 ml wells respectively covered by a tape from Abgene, part number AB-0718, and a closure with a porous plug 204 from Porex Corporation with part number 7724, but no airlock, where purging gas is introduced at a constant rate of approximately 20 ml/s. The lines 236 and 238 represent the evaporate loss from the same wells covered, respectively, by tape and the closure with a porous plug, where no gas is introduced. As can be seen in FIG. 6, the use of a closure with a porous plug significantly reduces the evaporative loss relative to the use of the tape.

The reduction of evaporation is advantageous as it limits any undesirable changes in the environment, e.g., from a concentration of salts or other material and/or the eventual termination of the reaction, due to a lack of water. Moreover, the porous plug 204 permits gasses to escape the well 110 easily, e.g., when overpressured, which is advantageous where gasses, such as $CO_2$ are produced during experiments. In addition, in microreactor 100 it is often desirable to control the environment of the sample 112 by introducing gasses such as $O_2$, $N_2$, $CO_2$, and $NH_3$. Gasses may be bubbled into the sealed well 110 with volumes of approximately 0.5 ml to 0.1 ml at a time. The porous plug 204 allows the introduced gasses to displace gas from the well volume. The porous plug 204 further retains the remaining gas in the headspace 114 of the well, after the overpressure has been relieved. Retention of the remaining gas in the headspace 114 is important as a primary method for introducing gasses into the sample 112 is via mixing with the headspace 114.

The one-way valve 206 is, by way of example, a tube 208 with a stop 210 that is normally closed, but that can be displaced to allow gas to flow in one direction. The stop 210 can be, e.g., a block or ball-bearing in the tube 208 that is held closed gravitationally, or a valve that is biased closed, e.g., with a spring, or other similar types of devices. A suitable one-way valve 206 can be purchased from Halkey Roberts of St. Petersburg, Fla., as part number 711ACL.

It may be desirable to maintain the wells 110 with a pressure that is greater than ambient by using, e.g., a spring loaded valve that requires a predetermined overpressure to release the gas. Such a one-way valve can be purchased from Halkey Roberts. The use of a spring loaded valve, or similar type of valve, to maintain an overpressure may be advantageous as gas transfer can be more effectively performed with overpressure. Moreover, many commercial systems either intentionally use overpressure, or naturally form an overpressure due to their depth. A pressurized microreactor is an effective way to simulate such a system. Further, an overpressure is an effective way to minimize back-flow into the well 110 and, thus, overpressure maintains a more controlled gas environment and helps with sterility.

The closure 200 may be manufactured, e.g., by inserting a one-way valve 206 into the cap 202 so the one-way valve 206 extends through the top and bottom of the cap 202. With the use of a pre-manufactured cap 202, it may be necessary to drill or punch a hole through the cap 202 prior to inserting the one-way valve 206. A porous plug 204 is inserted into the tube 208 of the one-way valve 206, e.g., at the bottom. In another embodiment, the one-way valve 206 is not used and the porous plug 204 itself is inserted through the cap 202 or into another tube without a valve. In general, the design and materials of the closure 200 should allow for sterilization. Gamma irradiation is a preferred means for sterilization. Alternative common sterilization means include e-beam irradiation, ethylene oxide, and autoclave. Where the porous plug 204 is formed from PTFE, ethylene oxide is the preferred means of sterilization as PTFE can be damaged by excessive irradiation.

The use of a closure 200 provides a sterile barrier, which prevents the contents of the well 110 from being contaminated by outside contaminants, and permits gas to be exchanged while reducing evaporative losses.

By way of comparison, a gas permeable membrane tape may be used to cover the top of the wells 110 of a microreactor 100. One suitable membrane is described in U.S. Ser. No. 10/777,581, filed on Feb. 11, 2004, having Publication No. 2005/0176155 and having the same assignee as the present disclosure and which is incorporated herein by reference. The gas permeable membrane tape provides a sterile barrier and does permit gas to be exchanged. However, the gas permeable membrane tape has a much greater evaporative loss, typical evaporation rate is 0.35 to 0.9 ml/day, and must be pealed back to sample the wells, which exposes the entire plate to potential contaminants, including wells not being sampled. Furthermore, as the gas permeable membrane tape forms a continuous sheet over the entire microreactor, there may be problems with cross-contamination, i.e., contaminants present in one well may be pushed onto the membrane tape and migrate to nearby wells. Accordingly, a closure, in accordance with an embodiment of the present invention, presents a superior device to seal a microreactor.

Figure 7:
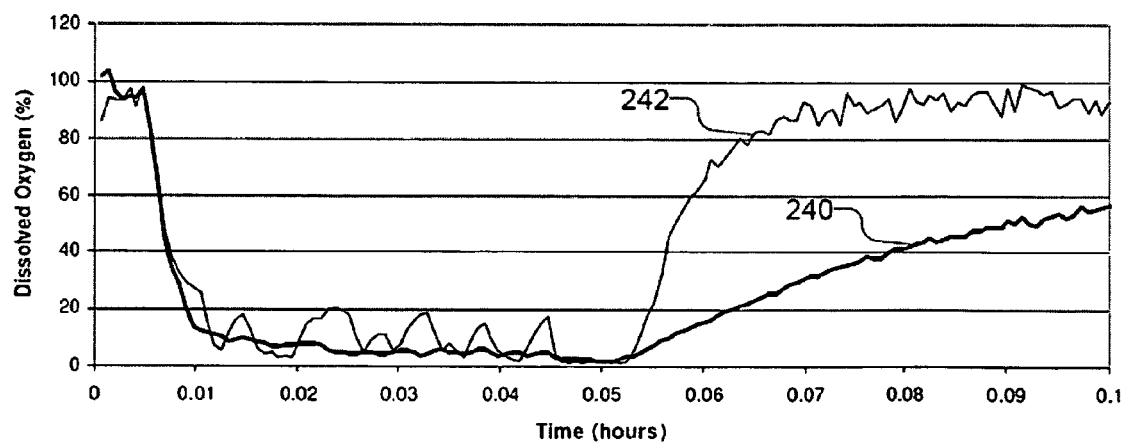
FIG. 7 is a graph illustrating the results of a series of experiments in which the dissolved oxygen in the well is measured as the well is purged with nitrogen.

Thus, the use of closure 200 enables the wells in a microreactor to be individually sealed, while reducing the evaporative loss compared to a conventional membrane tape. Further, the use of a one-way valve 206 with the closure 200 permits the venting of gas from within the well while gas, such as purging gas, to be introduced into the well. Moreover, the one-way valve minimizes or inhibits the back-flow of air into the well of the microreactor. Accordingly, an anaerobic environment may be formed in the microreactor well sealed with a closure 200 by purging the well, e.g., with nitrogen. The one-way valve 206 inhibits air from back-flowing into the well. FIG. 7 is a graph illustrating the results of an experiment in which the dissolved oxygen in the well is measured as the well is purged with nitrogen. Curve 240 illustrates the results for a well sealed with a closure having a porous plug and a one-way valve, as described above, while curve 242 illustrates the results for a well sealed with a closure with a porous plug and no one-way valve. FIG. 7 illustrates the superior performance of maintaining an anaerobic environment for systems with one-way valves compared to the systems with only porous plugs.

FIG. 8A illustrates a cross-sectional view of another cap 250 that may be used with the closure 200, in accordance with an embodiment of the present invention. Cap 250 includes a lower portion 252 that is inserted into the well 110. Cap 250 also includes an upper portion 254 that extends from the lower portion 252. Both the upper portion 254 and the lower portion 252 define a central aperture 256 that extends through the cap 250 into which a one-way valve can be inserted. FIG. 8B illustrates the cap 250 with a one-way valve 255 inserted through the central aperture 256. The upper portion 254 rises substantially above the lower portion 252, e.g., the upper portion 254 is approximately 50% to 150% of the height of the lower portion 252. The extended upper portion 254 assists in supporting the one-way valve 206, as well as simplifies in the handling of the closure, e.g., the upper portion 254 can be easily grasped when removing the closure from a well 110. Moreover, the extended upper portion 254 provides a better seal with the one-way valve 206 as there is greater surface area.

FIG. 9A illustrates another closure 300 in accordance with an embodiment of the present invention. The closure 300 may be manufactured from, e.g., rubber or silicon and includes a lower portion 302 and an upper portion 304, similar to that shown in FIG. 8. A porous plug 320 is inserted into the bottom of the aperture 306 that extends through the lower portion 302 and upper portion 304 of the closure 300. Porous plug 320 acts as the primary barrier to contamination and evaporation. The closure 300 may include an integrated one-way valve 310 including a ball 312 supported by a bevel 314 in the aperture 306. The ball 312, which may be, e.g., glass, is gravitationally held on the bevel 314. When gas is pushed from below, the ball 314 is pushed upward and the gas is allowed to escape. If desired, other types of valves may be used. A second porous plug 322 may be inserted into the top of the aperture 306 to act as a secondary barrier and to retain the ball 314 within the aperture. The ball 314 need not be used if desired, in which case, the closure 300 relies on the porous plugs 320 and/or 322 for barriers. Moreover, either the porous plug 322 or porous plug 320 may be removed if desired.

FIG. 9B illustrates a closure 350, which is similar to closure 300 shown in FIG. 9A, except closure 350 uses a gas porous membrane 352 instead of a porous plug 320. The membrane 352 may be a film of highly porous thin membrane through which gasses can be easily passed such as that in U.S. Ser. No. 10/777,581, filed on Feb. 11, 2004, having Publication No. 2005/0176155 and having the same assignee as the present disclosure and which is incorporated herein by reference. The membrane 352 may be manufactured from expanded PTFE (ePTFE) or other suitable material. The particular membrane 352 selected will depend on the desired permeability. The membrane 352 is attached to the closure 350, e.g., with a silicon pressure adhesive or other appropriate adhesive. Alternatively, the membrane 352 may be attached by ultrasonic or thermal bonding, such as that produced by Toman Tool Corporation.

The dimensions of the closure 300 are dependent on the type of microreactor it is to be used with. By way of example, for a 24 well microreactor with wells that have inner diameters of approximately 0.63 inches, the diameter $D_1$ of closure 300 may be approximately 0.579 inches, the angle θ is 11.35°, the height $H_1$ may be approximately 0.28 inches, while the height $H_2$ may be approximately 0.225 inches. The porous plugs 320 and 322 may be approximately 0.2 inches in height and 0.157 inches in diameter. The glass ball 312 may have a diameter of approximately 0.125 inches.

FIG. 10A illustrates another embodiment in which a plurality of closures 200 are coupled together to form a mat 400 that can cover one row of wells 110 in the microreactor 100, where each closure 402 still retaining its own independent relief system. If desired, additional closures 200 may be used to form a 2-dimensional array of closures 200 to cover at least a portion of the microreactor 100 or the entire microreactor 100, as illustrated by mat 400' in FIG. 10B. A mat 400 of closures may reduce manufacturing costs and may be faster to install in a microreactor 100.

Figure 11:
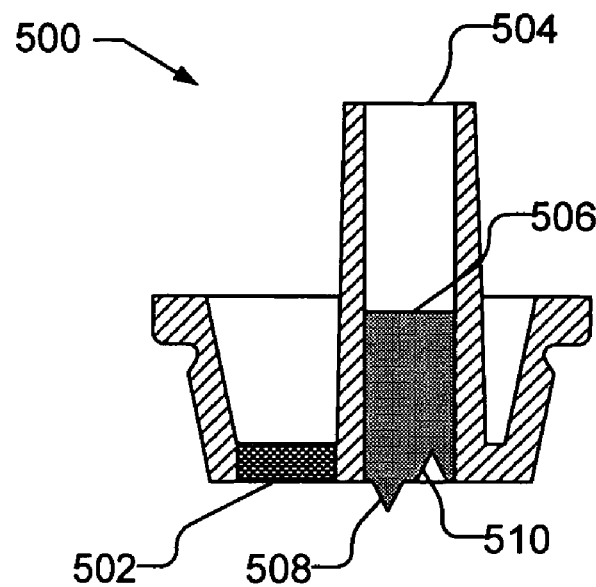
FIG. 11 illustrates another cap, in accordance with another embodiment of the present invention.

FIG. 11 illustrates a cap 500 in accordance with another embodiment of the present invention. Cap 500 is similar to cap 300, shown in FIG. 8, except that the cap 500 includes a septa 502. The septa 502 provides the ability to introduce and/or remove liquid from a well 110 without removing the cap 500. The septa 502, by way of example is a region of soft material, such as silicone that can be punctured with a thin tube (i.e. a syringe or a pipette tip) and then effective reseals after the tube is removed. The aperture 504, through which the one-way valve and/or the porous plug is inserted, is off center in cap 502 to make room for the septa 502. However, other configurations and septa mechanism may be used if desired. For example, "duck-bills" formed by two downward facing flaps of material can be used. The duck bills permit a tube to be pushed through and then reseal with the tube is removed. Alternatively, a miniature valve that can be opened or closed by a mechanical action, such as a push or a twist on an actuator point, can be used.

It should be understood that different types of experiments may require different types of closures. For example, when working with organisms that are "strict anaerobes" even a small amount of oxygen is sufficient to foul the experiment. In such a case, a closure that is most effective in maintaining a seal, such as a closure with a one-way valve or spring loaded valve should be used. Thus, different types of valves, porous plugs, and caps may be used as required by a particular experiment, and, in fact, within a single experiment multiple types of closures may be used.

Condensation can pose a challenge in the design of a microreactor and the closure, as the wells 110 of a microreactor 100 are sometimes heated to a temperature that is a few degrees warmer than the local environment. By way of example, it is often desired to conduct experiments at approximately ~37 degrees C. The closure may be at a temperature that is colder than the well and thus water will re-condense on the closure. Condensation can be problematic as it can block the gas pathway, e.g., by wetting the porous plug or fouling the one-way valve, as well as contaminate the pathways, e.g., the water can serve as a conduit for contamination. Further, condensation on the closure may result in the possible expulsion of the liquid, which represents an unwelcome source of water loss.

In order to minimize condensation, it is desirable for the porous plug, e.g., plug 204, to be as "non-wetting" as is possible. Both polyethylene and PTFE are non-wetting and are therefore good choices of material for the porous plug 204. It is noted that PTFE is more non-wetting and, thus, has an advantage over polyethylene. In addition, geometric features in the porous plugs may be used to naturally re-condense the liquid and allow the condensation to fall back into the well 110. FIG. 11, by way of example, illustrates a porous plug 506 with geometric features of an extension 508 and a depression 510 to assist in the re-condensation of liquid. It should be understood that the porous plug 506 may include many additional geometric features, which may all be of the same kind or may be a combination of features. Further, other geometric features may be used if desired. Another method of controlling condensation is to heat the closure relative to the well or to provide a "cold finger," which is an object deliberately stuck below the closure to condense the liquid and allow the liquid to fall back into the well 110.

Another challenge, which in part is related to condensation, is the clogging of the closure. Water or media can be deposited on the closure, e.g., from condensation or from foam caused by shaking the microreactor contents. The water or media can be pushed into the porous plug 204 or the one-way valve 206 by the gas pressure and act as a barrier to additional gas expulsion. Consequently, an overpressure is created, which can prevent additional gas from being introduced, as well as popping off the closure 200 and/or breaking the well 110 or possibly the microreactor 100. Accordingly, it is desirable to minimize clogging, e.g., by appropriate choice of materials or geometric design. By way of example, the use of PTFE for the porous plug is advantageous as more non-wetting. Geometric designs that include a large surface area of the porous plug 204, e.g., illustrated in FIG. 11, or that provide a barrier to liquid intrusion are advantageous. Alternatively, the formulation of the microreactor contents can be controlled to reduce clogging. For example, it would be desirable to reduce certain media additives, such as surfactants, that tend to make the liquid more prone to wet and penetrate porous plastics.

Figure 12:
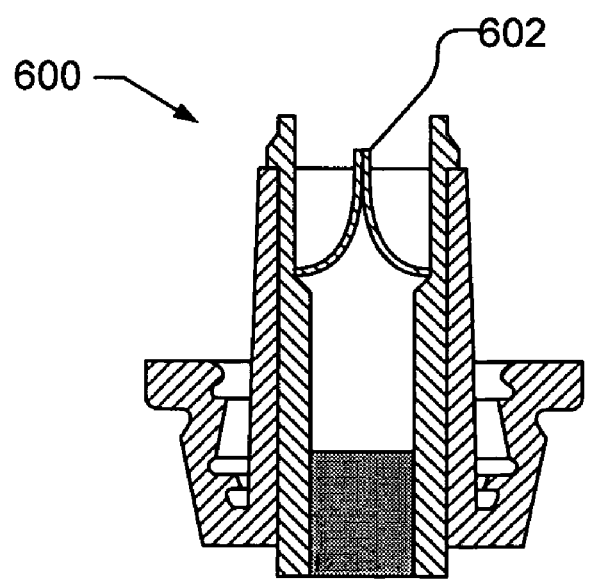
FIG. 12 illustrates another closure with a one-wave valve having a "duck-bill" configuration.

FIG. 12 illustrates another closure 600, which is similar to the closure 250 shown in FIGS. 8A and 8B, except the one-wave valve 602 has a "duck-bill" configuration, in which two flaps are biased towards each other into a closed position. Gas is permitted to escape by pushing the flaps of the duck-bill apart when there is an overpressure. Other one-wavy valves may be used if desired.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A closure for a microreactor having a plurality of 100 ml or smaller wells, each well having sidewalls, the closure comprising:
   a cap configured to be inserted into a 100 ml or smaller well of the microreactor, the cap having at least a portion that is compliant to form a seal with the sidewalls of the well when inserted, the cap having an aperture extending from a bottom surface of the cap to a top surface of the cap; and
   a tube inserted in the aperture in the cap and a porous plug inserted in the tube, the porous plug configured to permit gas within the well to pass through the aperture in the cap while reducing the amount of liquids and microbes that pass through the aperture in the cap.

2. The closure of claim 1, further comprising at least one of a septa, a duck-bill and a mechanically actuated valve in the cap through which material can be added to and removed from the well in which the cap is inserted.

3. The closure of claim 2, wherein the septa is a region of soft material in the cap through which a tube can be inserted, the soft material resealing after the tube is removed.

4. The closure of claim 1, wherein the porous plug has a porosity of between 0.2 μm and 50 μm.

5. The closure of claim 1, wherein the porous plug has a porosity of less than 0.2 μm.

6. The closure of claim 1, wherein the porous plug is manufactured from at least one of polyethylene, polypropylene, polytetrafluoroethylene, Polyvinylidene Fluoride, polyamines, and polyurethane.

7. The closure of claim 1, further comprising a plurality of caps coupled together, each one of the plurality of caps being configured to be inserted into a 100 ml or smaller well of the microreactor, each cap having an aperture extending from a bottom surface to a top surface; and a plurality of porous plugs each of which is coupled to an aperture in a different cap.

8. A closure for a microreactor having a plurality of 100 ml or smaller wells, each well having sidewalls, the closure comprising:
- a cap configured to be inserted into a 100 ml or smaller well of the microreactor, the cap having at least a portion that is compliant to form a seal with the sidewalls of the well when inserted, the cap having an aperture extending from a bottom surface of the cap to a top surface of the cap; and
- a tube inserted in the aperture in the cap and a porous plug inserted in the tube, the porous plug on figured to permit gas within the well to pass through the aperture in the cap while reducing the amount of liquids and microbes that pass through the aperture in the cap,
- the closure further comprising a one-way valve inserted into the tube, the one-way valve configured to permit gas within the well to pass through the aperture in the cap while inhibiting gas from outside the well to pass through the aperture in the cap.

9. The closure of claim 8, wherein the one-way valve is one of a spring loaded valve, a gravitationally held valve, and a duck-bill valve.

10. The closure of claim 5, wherein the porous plug is manufactured from at least one of polyethylene, polypropylene, polytetrafluoroethylene, Polyvinylidene Fluoride, polyamines, and polyurethane.

11. A closure for a microreactor having a plurality of 100 ml or smaller wells, each well having sidewalls, the closure comprising:
- a cap configured to be inserted into a 100 ml or smaller well of the microreactor, the cap having at least a portion that is compliant to form a seal with the sidewalls of the well when inserted the cap having an a aperture extending from a bottom surface of the cap to a top surface of the cap; and
- a first porous plug coupled to the aperture in the cap near the bottom surface of the cap, the porous plug configured to permit gas within the well to pass through the aperture in the cap while reducing the amount of liquids and microbes that pass through the aperture in the cap,
- the closure further comprising a second porous plug coupled to the aperture in the cap near the top surface of the cap;
- the closure further comprising a one-way valve coupled to the aperture in the cap and disposed between the first porous plug and the second porous plug.

12. The closure of claim 11, wherein the porous plug is manufactured from at least one of polyethylene, polypropylene, polytetrafluoroethylene, Polyvinylidene Fluoride, polyamines, and polyurethane.

13. A closure for a microreactor having a plurality of 100 ml or smaller wells, each well having sidewalls, the closure comprising:
- a cap configured to be inserted into a 100 ml or smaller well of the microreactor, the cap having at least a portion that is compliant to form a seal with the sidewalls of the well when inserted, the cap having an aperture extending from a bottom surface of the cap to a top surface of the cap; and
- a porous plug coupled to the aperture in the cap, the porous plug configured to permit gas within the well to pass through the aperture in the cap while reducing the amount of liquids and microbes that pass through the aperture in the cap, wherein the porous plug includes geometric features on a bottom surface, the geometric features being one of an extension and a depression in the porous plug.

14. The closure of Claim 13, wherein the porous plug is inserted in the aperture in the cap.

15. The closure of claim 13, wherein the porous plug is manufactured from at least one of polyethylene and polytetrafluoroethylene.

16. An apparatus for sealing the wells of a microreactor, the wells having sidewalls, the apparatus comprising:
- a cap having flexible outer sidewalls that are configured to contact and form a seal with the sidewalls of a well of the microreactor, the cap having an aperture extending from a bottom surface of the cap to a top surface of the cap;
- a tube inserted in the aperture in the cap and a porous plug and a one-way valve inserted in the tube, the porous plug configured to permit gas within the well to pass through the aperture in the cap; and
- the one-way valve configured to permit gas within the well to pass through the aperture in the cap while inhibiting gas from outside the well to pass through the aperture in the cap.

17. The apparatus of claim 16, wherein the porous plug is inserted in the one-way valve.

18. An apparatus for sealing the wells of a microreactor, the wells having sidewalls, the apparatus comprising:
- a cap having flexible outer sidewalls that are configured to contact and form a seal with the sidewalls of a well of the microreactor, the cap having an aperture extending from a bottom surface of the cap to a top surface of the cap;
- a first porous plug coupled to the aperture in the cap, the porous plug configured to permit gas within the well to pass through the aperture in the cap;
- a second porous plug; and
- a one-way valve coupled to the aperture in the cap, the one-way valve configured to permit gas within the well to pass through the aperture in the cap while inhibiting gas from outside the well to pass through the aperture in the cap; wherein the one-way valve is disposed between the first porous plug and the second porous plug.

19. A closure for a microreactor having a plurality of 100 ml or smaller wells, each well having sidewalls, the closure comprising:
- a cap configured to be inserted into a 100 ml or smaller well of the microreactor, the cap having at least a portion that is compliant to form a seal with the sidewalls of the well when inserted, the cap having an aperture extending from a bottom surface of the cap to a top surface of the cap; and
- a tube inserted in the aperture in the cap and a one-way valve inserted in the tube, the one-way valve configured to permit gas within the well to pass through the aperture in the cap while inhibiting gas from outside the well to pass through the aperture in the cap.

20. The closure of claim 19, wherein the aperture is covered by a gas porous membrane film.

21. The closure of claim 19, wherein the one-way valve is one of a spring loaded valve, a gravitationally held valve, and a duck-bill valve.

22. A method comprising:
- providing a microreactor having a plurality of wells, each well having a volume of 100 ml or less;
- providing at least one closure with a one-way valve; and
- sealing at least one well of the microreactor with the at least one closure with the one-way valve, the one-way valve permitting gas within the well to escape while inhibiting gas from outside the well to enter the well; and,
- venting the gas inside the well through the one-way valve while purging gas is introduced into the well.

23. The method of claim 22, wherein the provided closure also includes a sterile barrier that inhibits evaporative losses.

* * * * *